(12) United States Patent
Lee et al.

(10) Patent No.: US 11,052,012 B2
(45) Date of Patent: Jul. 6, 2021

(54) PELVIS FIXING DEVICE AND MOTION ASSISTANCE APPARATUS INCLUDING THE SAME

(71) Applicant: Samsung Electronics Co., Ltd., Suwon-si (KR)

(72) Inventors: Jongwon Lee, Suwon-si (KR); Minhyung Lee, Anyang-si (KR); Youn Baek Lee, Yongin-si (KR); Jeonghun Kim, Hwaseong-si (KR); Se-Gon Roh, Suwon-si (KR); Byungjune Choi, Gunpo-si (KR); Hyun Do Choi, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 634 days.

(21) Appl. No.: 15/066,742

(22) Filed: Mar. 10, 2016

(65) Prior Publication Data

US 2017/0056276 A1    Mar. 2, 2017

(30) Foreign Application Priority Data

Aug. 26, 2015 (KR) .......................... 10-2015-0119962

(51) Int. Cl.
*A61H 3/00* (2006.01)
*B25J 9/00* (2006.01)
(Continued)

(52) U.S. Cl.
CPC ............. *A61H 3/00* (2013.01); *A61F 5/0102* (2013.01); *A61F 5/0193* (2013.01);
(Continued)

(58) Field of Classification Search
CPC ....... A41F 9/00; A41F 9/025; A41D 13/0525; A41D 13/0537; Y10T 403/32426;
(Continued)

(56) References Cited

U.S. PATENT DOCUMENTS 1,031,142 A * 7/1912 Miller ....................... A41F 9/00
 2/236
3,351,053 A * 11/1967 Stuttle ..................... A61F 5/024
 602/19

(Continued)

FOREIGN PATENT DOCUMENTS

CN    203539644 U    4/2014
CN    104000708 A    8/2014
(Continued)

OTHER PUBLICATIONS

Extended European Search Report dated Feb. 21, 2017 for corresponding EP Application No. 16175675.4.
(Continued)

*Primary Examiner* — Timothy A Stains
*Assistant Examiner* — Matthew R Moon
(74) *Attorney, Agent, or Firm* — Harness, Dickey & Pierce, P.L.C.

(57) ABSTRACT

Provided is a pelvis fixing device including a rear fixing module including a driving module mounting portion, the rear fixing portion configured to enclose a side surface and a rear surface of a waist of a user, and a front fixing module including a soft layer and a hard layer configured to enclose a front surface of the waist of the user, wherein the hard layer is connected to the rear fixing module to form a closed loop around the waist of the user.

14 Claims, 13 Drawing Sheets

(51) Int. Cl.
*A61H 1/02* (2006.01)
*A61F 5/01* (2006.01)
*G16H 20/30* (2018.01)
*G16H 10/60* (2018.01)

(52) U.S. Cl.
CPC .......... *A61H 1/0244* (2013.01); *B25J 9/0006* (2013.01); *G16H 10/60* (2018.01); *G16H 20/30* (2018.01); *A61H 2003/007* (2013.01); *A61H 2201/0107* (2013.01); *A61H 2201/0192* (2013.01); *A61H 2201/1207* (2013.01); *A61H 2201/164* (2013.01); *A61H 2201/165* (2013.01); *A61H 2201/1628* (2013.01); *A61H 2201/1642* (2013.01); *A61H 2201/1676* (2013.01); *A61H 2201/5007* (2013.01); *A61H 2201/5012* (2013.01); *A61H 2201/5015* (2013.01); *A61H 2201/5048* (2013.01)

(58) Field of Classification Search
CPC .......... Y10T 403/32434; A61H 1/00; A61H 1/0214; A61H 1/0237; A61H 1/0244; A61H 1/0255; A61H 1/0262; A61H 2001/0211; A61H 2001/165; A61H 2001/1652; A61H 2001/0203; A61H 2001/024; A61H 2001/0266; A61H 2001/0274; A61H 2001/0277; A61H 2001/0281; A61H 2001/0285; A61H 2205/088; A61H 2205/10; A61H 2205/108; A61F 5/02; A61F 5/022; A61F 5/024; A61F 5/026; A61F 5/028; A61F 5/0102; A61F 5/0585; A61F 5/0123
See application file for complete search history.

(56) References Cited

U.S. PATENT DOCUMENTS

| | | | | | |
|---|---|---|---|---|---|
| 3,407,818 | A | * | 10/1968 | Costanzo | A61F 7/007 219/211 |
| 4,761,834 | A | * | 8/1988 | Kolb | A41D 13/0506 2/267 |
| 5,129,647 | A | * | 7/1992 | Castellanos | A63B 21/055 482/124 |
| 5,152,443 | A | * | 10/1992 | Hagan | A41F 9/002 224/148.4 |
| 5,363,863 | A | * | 11/1994 | Belli | A61F 5/028 128/876 |
| 5,378,225 | A | * | 1/1995 | Chatman, Jr. | A61F 5/028 219/480 |
| 5,394,571 | A | * | 3/1995 | Vernon | A61G 9/003 4/450 |
| 5,690,609 | A | * | 11/1997 | Heinze, III | A61F 5/028 128/115.1 |
| 5,830,168 | A | | 11/1998 | Finnell et al. | |
| 6,533,739 | B1 | * | 3/2003 | Palmer | A61F 5/03 601/41 |
| 8,221,339 | B2 | | 7/2012 | Hirata et al. | |
| 8,545,424 | B2 | | 10/2013 | Hirata et al. | |
| 9,216,130 | B2 | * | 12/2015 | Killian | A61H 1/0244 |
| 2003/0181839 | A1 | * | 9/2003 | Bremer | A61F 5/055 602/19 |
| 2005/0111174 | A1 | * | 5/2005 | Jordan | G09F 21/02 361/679.03 |
| 2006/0258967 | A1 | * | 11/2006 | Fujil | A61F 5/0102 602/23 |
| 2008/0262401 | A1 | * | 10/2008 | Wagner | A61F 5/028 602/19 |
| 2009/0306554 | A1 | | 12/2009 | Yasuie | |
| 2011/0160626 | A1 | * | 6/2011 | Takahashi | A61H 1/0244 601/34 |
| 2011/0218466 | A1 | | 9/2011 | Takahashi et al. | |
| 2012/0316477 | A1 | * | 12/2012 | Hamaya | H01M 2/1066 601/35 |
| 2013/0021788 | A1 | * | 1/2013 | Mayes | G09F 13/00 362/183 |
| 2014/0161554 | A1 | * | 6/2014 | Ewasko | B60P 3/062 410/2 |
| 2014/0212243 | A1 | * | 7/2014 | Yagi | A61H 3/00 414/2 |
| 2016/0025186 | A1 | * | 1/2016 | DeLuca | F16G 11/103 24/130 |
| 2017/0049659 | A1 | * | 2/2017 | Farris | B25J 9/104 |

FOREIGN PATENT DOCUMENTS

| | | |
|---|---|---|
| EP | 1 637 115 A1 | 3/2006 |
| JP | 5101470 B2 | 12/2012 |
| JP | 2013173190 A | 9/2013 |
| JP | 2015058015 A | 3/2015 |
| KR | 100612031 B1 | 8/2006 |
| KR | 10-1141905 B1 | 5/2012 |
| WO | WO-2014/057410 A1 | 4/2014 |

OTHER PUBLICATIONS

Chinese Office Action dated Aug. 23, 2019 for CN Patent Application No. 201610357768.3 (with English translation).

\* cited by examiner

PELVIS FIXING DEVICE AND MOTION ASSISTANCE APPARATUS INCLUDING THE SAME

CROSS-REFERENCE TO RELATED APPLICATION

This application claims under 35 U.S.C. § 119 to Korean Patent Application No. 10-2015-0119962, filed on Aug. 26, 2015, in the Korean Intellectual Property Office, the entire contents of which are incorporated herein by reference in its entirety.

BACKGROUND

1. Field

At least one example embodiment relates to a pelvis fixing device and/or a motion assistance apparatus including the same.

2. Description of the Related Art

With the onset of rapidly aging societies, a number of people are experiencing inconvenience and/or pain from joint problems. Thus, there may be a growing interest in motion assistance apparatuses enabling the elderly and/or patients having joint problems to walk with less effort. Furthermore, motion assistance apparatuses increasing muscular strength of human bodies may be desired for military purposes.

SUMMARY

Some example embodiments relate to a pelvis fixing device.

In some example embodiments, the pelvis fixing device may include a rear fixing module including a driving module mounting portion, the rear fixing portion configured to enclose a side surface and a rear surface of a waist of a user, and a front fixing module including a soft layer and a hard layer configured to enclose a front surface of the waist of the user. The hard layer may be connected to the rear fixing module to form a closed loop around the waist of the user.

The hard layer may be rigid in a vertical direction and flexible in a back-and-forth direction relative to the waist of the user.

The rear fixing module may include a back supporting portion configured to support a back of the user, and a pair of rigid frames, each including the driving module mounting portion, configured to connect both ends of the back supporting portion to both ends of the hard layer.

The soft layer may include a first soft band and a second soft band, and one side of each of the first soft band and the second soft band may be attached to the rear fixing module, and another side of one of the first soft band and the second soft band is detachable from another side of the other of the first soft band and the second soft band.

The hard layer may include a fixing plate disposed at a center of the soft layer, and a unidirectional flexible plate to be connected to or disconnected from the fixing plate.

The unidirectional flexible plate may be rigid in a direction vertical to the ground and flexible in a direction horizontal to the ground based on a state in which the user is standing erect.

The unidirectional flexible plate may include a flexible plate body of which one end is connected to the rear fixing module, and another end is configured to extend lengthwise along the soft layer, and a flexible plate rib configured to elongate in a direction perpendicular to a longitudinal direction of the flexible plate body.

The hard layer may further include a length adjusting portion provided in the fixing plate to adjust a fastening length of the unidirectional flexible plate.

The unidirectional flexible plate may include a plurality of flexible plate ribs disposed to be spaced apart from each other in the longitudinal direction of the flexible plate body, the length adjusting portion may include a hanging portion to be connected to at least one of the flexible plate ribs, and the fastening length of the unidirectional flexible plate may be adjusted based on a position at which the hanging portion is connected.

The pelvis fixing device may further include a battery disposed on a front surface of the fixing plate.

The fixing plate may include a seating space in which the battery is seated, and a battery attaching and detaching portion provided on one side of the seating space. The battery may be attachable to and detachable from the battery attaching and detaching portion in a snap fastening manner.

The front fixing module may further include a fixing plate, and the battery may be detachable from the fixing plate.

The fixing plate may be formed to be disposed at a center of the front surface of the user.

The hard layer may include a unidirectional flexible plate to be inserted in the soft layer.

The pelvis fixing device may further include a flexible plate supporting portion configured to support the unidirectional flexible plate so that the unidirectional flexible plate slides in a longitudinal direction of the soft layer.

The flexible plate supporting portion may include a fabric tunnel provided in the longitudinal direction of the soft layer, and a plurality of stiffeners disposed to be spaced apart from each other in a longitudinal direction of the fabric tunnel. The unidirectional flexible plate may be inserted in the fabric tunnel.

The soft layer may include a lining to be in close contact with the front surface of the user, an upper configured to enclose the lining, and formed using a material with a less flexibility than the lining, and a battery fastening portion provided on the upper. The battery may be fastened with the battery fastening portion.

The upper may include a first inserting slot in which the unidirectional flexible plate is to be inserted, and the first inserting slot may be connected to an entrance portion of the fabric tunnel.

The upper may further include a second inserting slot connected to an exit portion of the fabric tunnel, and the pelvis fixing device may further include an additional fastening portion configured to connect the unidirectional flexible plate to the rear fixing module through the second inserting slot.

The pelvis fixing device may further include an iliac crest pad connected between the rear fixing module and the front fixing module.

The iliac crest pad may include a pad body to be in close contact with an iliac crest of the user, a first connecting portion hinge-connected to the driving module mounting portion, and a second connecting portion detachable from the front fixing module.

Other example embodiments relate to a motion assistance apparatus.

In some example embodiments, the motion assistance apparatus may include a driving module configured to generate a power to assist a motion of a user, a supporting module connected to the driving module to support a portion of the user, and a pelvis fixing device including a rear fixing module including a driving module mounting portion in which the driving module is to be mounted, and a front fixing module including a soft layer and a hard layer connected to both ends of the rear fixing module, the soft layer and the hard layer having different rigidnesses. The hard layer may be connected to the rear fixing module to form a closed loop around a waist of the user.

The hard layer may include a unidirectional flexible plate which is rigid in a direction vertical to the ground and flexible in a direction horizontal to the ground based on a state in which the user is standing erect.

At least one example embodiment relates to a fixing device.

In some example embodiments, the fixing device may include a two-piece waist band configured to enclose a waist of a user and support at least one driver mounted thereto, the two-piece waist band including, a front waist band having a dual layer structure including an inner soft layer and an outer hard layer, the inner soft layer configured to contact the wearer and the outer hard layer configured to suppress deformation of the front waist band due in response to torque generated by the at least one driver, and a rear waist band configured to connect to the outer hard layer to form a closed loop around the waist of the user.

In some example embodiments, the rear waist band includes a back support configured to support a back of the user; and at least two rigid frames configured to connect first and second ends of the back support to first and second ends of the hard outer layer, respectively, to form the closed loop around the waist of the user.

In some example embodiments, the outer hard layer of the front waist band includes two straps each having a first end and a second end, the first end of each of the two straps being connected to the rear waist band and the second end of each of the two straps having a plurality of flexible ribs therein spaced apart from each other in a longitudinal direction.

In some example embodiments, the front waist band further includes a fastener configured to connect to one of the plurality of flexible ribs in each of the two straps such that a circumference of two-piece waist band varies based on which of the plurality of flexible ribs is connected to the fastener.

In some example embodiments, the fastener is configured to hold a battery on a surface thereof such that the battery is at a front of the waist of the user, the battery configured to provide power to the at least one driver.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
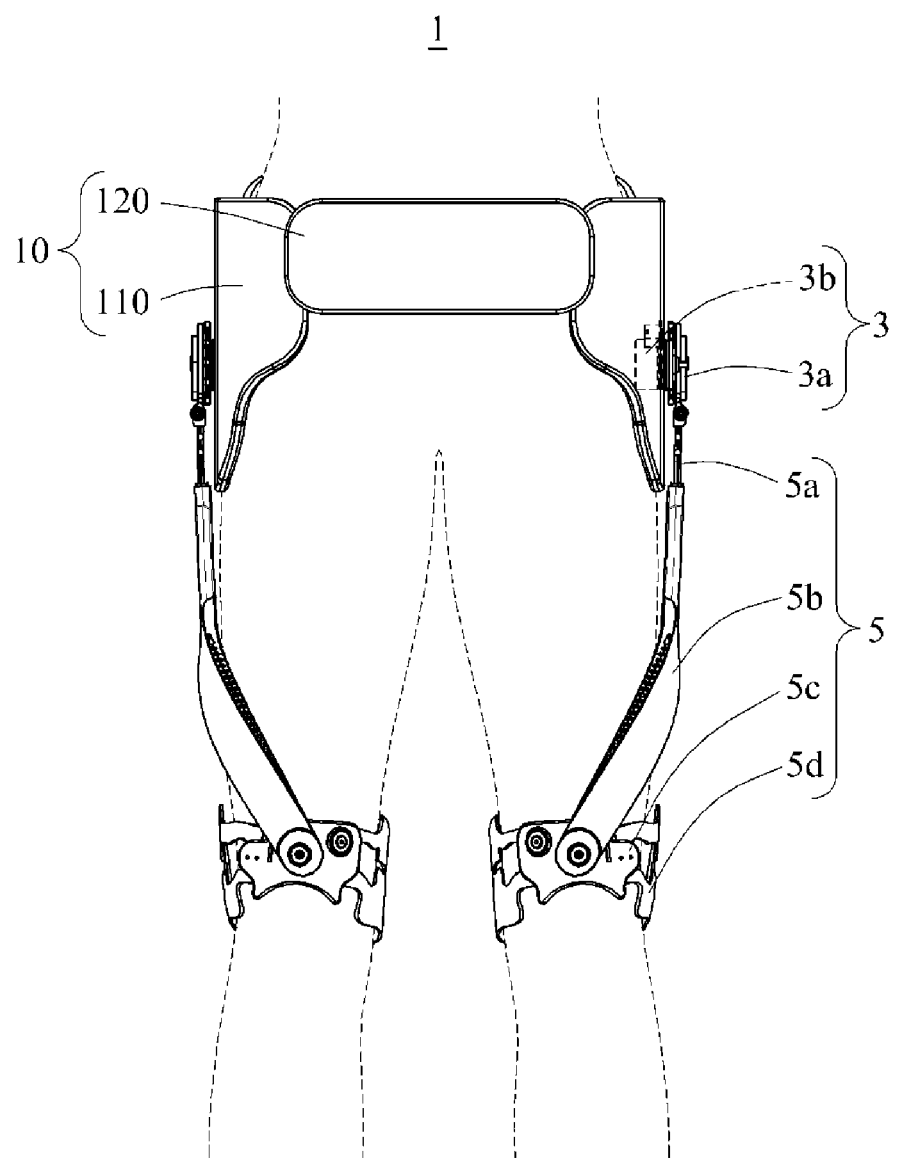
FIG. 1 is a front view illustrating a motion assistance apparatus according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. Terms, such as those defined in commonly used dictionaries, should be interpreted as having a meaning that is consistent with their meaning in the context of the relevant art and/or this disclosure, and should not be interpreted in an idealized or overly formal sense unless expressly so defined herein.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as one computer processing device; however, one skilled in the art will appreciate that a hardware device may include multiple processing elements and multiple types of processing elements. For example, a hardware device may include multiple processors or a processor and a controller. In addition, other processing configurations are possible, such as parallel processors.

Various example embodiments will now be described more fully with reference to the accompanying drawings in which some example embodiments are shown. In the drawings, the thicknesses of layers and regions are exaggerated for clarity.

Figure 2:
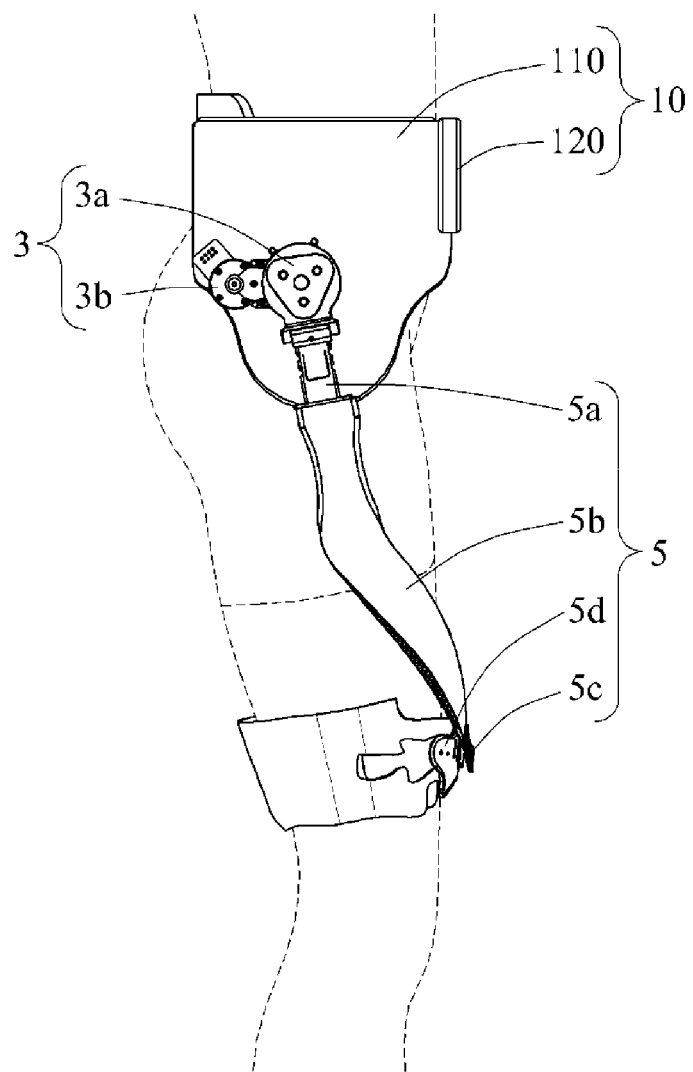
FIG. 2 is a side view illustrating a motion assistance apparatus according to at least one example embodiment.

FIG. 1 is a front view illustrating a motion assistance apparatus according to at least one example embodiment, and FIG. 2 is a side view illustrating the motion assistance apparatus according to at least one example embodiment.

Referring to FIGS. 1 and 2, a motion assistance apparatus 1 may be worn by a user to assist a motion of the user.

The user may correspond to a human, an animal, or a robot. However, the user is not limited thereto. The motion assistance apparatus 1 may assist a motion of a part of the user. For example, as illustrated in FIG. 1, in some example embodiments, the motion assistance apparatus 1 may assist motions of thighs of the user. However, example embodiments are not limited thereto and the motion assistance apparatus 1 may assist other portions of the user's body in addition to or in lieu of assisting the thighs of the user. For example, the motion assistance apparatus 1 may assist a motion of an upper body, for example, a hand, an upper arm, and/or a lower arm of the user. Further, the motion assistance apparatus 1 may assist a motion of another part of a lower body other than the thighs, for example, a foot, and/or a calf of the user.

Hereinafter, a case in which the motion assistance apparatus 1 assists motions of thighs of a human will be described. However, example embodiments are not limited thereto.

The motion assistance apparatus 1 may include a fixing device 10, a driving module 3, a supporting module 5, a controller configured to control the driving module 3, and a battery configured to supply a power to the driving module 3. In some example embodiments, the fixing device 10 may be a pelvis fixing device 10.

The pelvis fixing device 10 may be fixed to one or more sides of a waist of the user, and include a curved surface corresponding to a contact portion of the user. The pelvis fixing device 10 may include a rear fixing module 110 configured to enclose a side surface and a rear surface of the waist of the user, and a front fixing module 120 configured to enclose a front surface of the waist of the user.

The driving module 3 may provide a power to be transmitted to the supporting module 5. The driving module 3 may include an actuator 3b configured to receive a voltage or a current from the battery and generate a power, and a joint assembly 3a disposed at a position corresponding to a hip joint to transmit the power generated by the actuator 3b to the supporting module 5.

For example, the actuator 3b may be disposed in a lateral direction of the joint assembly 3a, in detail, such that a rotation axis of the actuator 3b may be spaced apart from a rotation axis of the joint assembly 3a. In this example, when compared to a case in which the actuator 3b and the joint assembly 3a share a rotation axis, a protruding height from the user may decrease. Dissimilar to the drawings, the actuator 3b may be more spaced apart from the joint assembly 3a. For example, the actuator 3b may be disposed on one side of the rear fixing module 110. In this example, a power transmitting module may be additionally provided to transmit a power from the actuator 3b to the joint assembly 3a. The power transmitting module may be a rotary body such as, for example, a gear, or a longitudinal member such as, for example, a wire, a cable, a string, a rubber band, a spring, a belt, and a chain.

The supporting module 5 may support a lower limb of the user, for example, a thigh of the user, and assist a motion of the lower limb. The supporting module 5 may rotate using a torque of the driving module 3. The supporting module 5 may include a connecting member 5a, a force transmitting frame 5b, an applying member 5c, and a supporting member 5d.

The connecting member 5a may be hinge connected to, for example, the joint assembly 3a. A hinge axis of the connecting member 5a may be disposed in a direction intersecting with, for example, orthogonal to, the rotation axis of the joint assembly 3a. In this example, the supporting module 5 may perform a two degree of freedom (DOF) motion with respect to the pelvis fixing device 10.

The force transmitting frame 5b may transmit a force to a portion of the user. A first end portion of the force transmitting frame 5b may be rotatably connected to the connecting member 5a, and a second end portion of the force transmitting frame 5b may be connected to the applying member 5c to transmit a force to a portion of the user. For example, the force transmitting frame 5b may push or pull the thigh of the user. The force transmitting frame 5b may extend in a longitudinal direction of the thigh of the user, and be bent to enclose a portion of a circumference of the thigh of the user. The first end portion of the force transmitting frame 5b may be disposed on a side surface of the thigh of the user, and the second end portion of the force transmitting frame 5b may be disposed on a front surface of the thigh of the user. In detail, a surface on the side of the first end portion of the force transmitting frame 5b may be orthogonal to a surface on the side of the second end portion of the force transmitting frame 5b.

The force transmitting frame 5b may be movably connected to the connecting member 5a. By relative motions of the force transmitting frame 5b and the connecting member 5a, a total length from the joint assembly 3a to the applying member 5c may be variable. In this example, the supporting module 5 may perform a three DOF motion with respect to the pelvis fixing device 10.

The applying member 5c may be connected to the second end portion of the force transmitting frame 5b to apply a force to a portion of the user. For example, the applying member 5c may be disposed along the front surface of the thigh of the user, or in a circumferential direction of the thigh of the user to push or pull the thigh of the user. The applying member 5c may include a curved surface corresponding to the thigh of the user, and configured to extend from the second end portion of the force transmitting frame 5b toward both sides of the force transmitting frame 5b.

The supporting member 5d may be connected to one side of the applying member 5c. For example, the supporting member 5d may be disposed to enclose a circumference of the thigh of the user, thereby preventing a separation of the thigh of the user from the force transmitting frame 5b.

Meanwhile, a driving module and/or a supporting module may be additionally provided. For example, in some example embodiments, the supporting module 5 may extend to a knee, and an additional joint assembly may be provided in the supporting module 5 at a position corresponding to a knee joint. Further, an additional supporting module may be connected to the additional joint assembly. The additional supporting module may support a calf of the user, thereby assisting a motion of the calf. Here, an actuator configured to drive the additional joint assembly may be disposed on one side of the additional joint assembly, or may be disposed in, for example, the rear fixing module 110 to be spaced apart from the additional joint assembly.

The controller (not shown) may include a memory and a processor.

The memory may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

The processor may be implemented by at least one semiconductor chip disposed on a printed circuit board. The processor may be an arithmetic logic unit, a digital signal processor, a microcomputer, a field programmable array, a programmable logic unit, a microprocessor or any other device capable of responding to and executing instructions in a defined manner. The processor may be programmed with instructions that configure the processor into a special purpose computer to control the driving module 3 to assist the user with walking.

Figure 3:
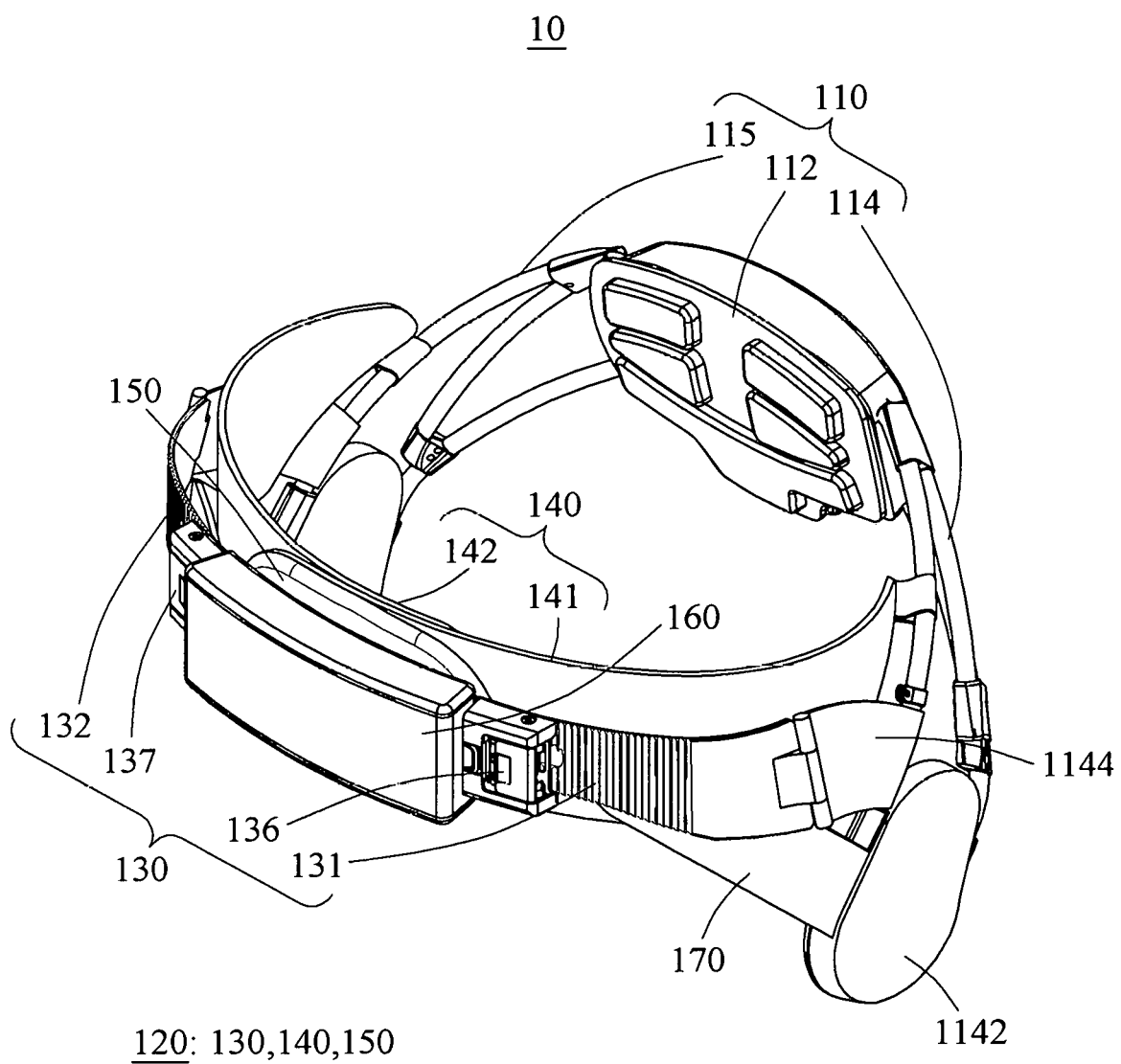
FIG. 3 is a perspective view illustrating a pelvis fixing device according to at least one example embodiment.

FIG. 3 is a perspective view illustrating a pelvis fixing device according to at least one example embodiment.

Referring to FIG. 3, the pelvis fixing device 10 may include the rear fixing module 110 configured to enclose a side surface and a rear surface of a waist of a user, the front fixing module 120 configured to enclose a front surface of the waist of the user, a battery 160, and an iliac crest pad 170 connected between the rear fixing module 110 and the front fixing module 120.

The rear fixing module 110 may include a back supporting portion 112 configured to support a back of the user, a first rigid frame 114, and a second rigid frame 115. The first rigid frame 114 and the second rigid frame 115 may be connected to the back supporting portion 112 and configured to extend from the back supporting portion 112 toward both sides along the side surface and the rear surface of the waist of the user. Hereinafter, unless otherwise mentioned, descriptions related to the first rigid frame 114 may be applicable to the second rigid frame 115.

In some example embodiments, the back supporting portion 112 may be formed using a soft material to be in close contact with a perimeter of the back of the user, thereby, for example, increasing wearability.

The first rigid frame 114 may be connected to the back supporting portion 112, and formed using a rigid material. The first rigid frame 114 may include, for example, a rod-shaped longitudinal member. The longitudinal member may be provided in a form of a hollow tube. In the foregoing structure, the pelvis fixing device 10 may have a sufficient rigidity while the weight of the pelvis fixing device 10 may be reduced. The first rigid frame 114 may include a driving module mounting portion 1142, and a hinge portion 1144. Likewise, the second rigid frame 114 may include a driving module mounting portion 1152, and a hinge portion 1154.

The driving module 3 of the motion assistance apparatus 1 may be disposed in the driving module mounting portion 1142. The driving module mounting portion 1142 may be provided, for example, in a portion corresponding to a position of a hip joint of the user. For example, the driving module mounting portion 1142 may be disposed in a space surrounded by the rod-shaped longitudinal member.

The hinge portion 1144 may rotatably connect the first rigid frame 114 to the front fixing module 120. One side of the hinge portion 1144 may be fixed to the first rigid frame 114, and another side of the hinge portion 1144 may be rotatably connected to the front fixing module 120.

A rotation axis of the hinge portion 1144 may be disposed in a direction orthogonal to a rotation axis of the driving module 3. Further, the rotation axis of the hinge portion 1144 may be disposed to be spaced apart from the rotation axis of the driving module 3 so that an extension line of the rotation axis of the hinge portion 1144 may not meet an extension line of the rotation axis of the driving module 3. In the foregoing arrangement, a movement of the driving module 3 may be decoupled from relative movements between the hinge portion 1144 and the front fixing module 120. Therefore, a rotation of the front fixing module 120 with respect to the hinge portion 1144 in response to an operation of the driving module 3 may be prevented.

The rotation axis of the hinge portion 1144 may correspond to a direction vertical to the ground, for example, a vertical direction in FIG. 3, based on a state in which the user wearing the pelvis fixing device 10 is standing erect. In the foregoing arrangement, a shape of at least a portion of the front fixing module 120 may be deformed suitably for a body shape of the user. In detail, when a large or paunchy user wears the pelvis fixing device 10, the front fixing module 120 may protrude frontward, whereby wearability for the user may increase.

The front fixing module 120 may include a hard layer 130, a soft layer 140 to be in close contact with the front surface of the waist of the user, and a layer fastening portion 150 configured to fasten the hard layer 130 with the soft layer 140.

Both ends of the soft layer 140 may be connected to the rear fixing module 110 and a central portion of the soft layer 140 may be connected to the hard layer 130. The soft layer 140 may be detachable to increase wearability for the user. A length of the soft layer 140 may be adjustable so that the soft layer 140 may be in close contact with the front surface of the waist of the user suitably for the body shape of the user. The soft layer 140 may include a first soft band 141 and a second soft band 142 that are detachable from each other.

The hard layer 130 may be rigid in a vertical direction and flexible in a back-and-forth direction relative to the waist of the user. The hard layer 130 and the rear fixing module 110 may form a closed loop around the waist of the user. In the foregoing structure, a distortion of the rear fixing module 110 caused by a torque generated by the driving module 3 may be prevented. In detail, when the user performs a walking motion, driving modules 3 provided on both sides of the motion assistance apparatus 1 may rotate in opposite directions. Both ends of the rear fixing module 110 may alternately move up and down. Thus, each of the ends of the rear fixing module 110 may experience forces that can cause distortions. However, since the rear facing module 110 and the hard layer 130 of the front fixing module 120 are in a closed loop structure as described above, torques transmitted to both ends of the rear fixing module 110 may offset each other at a central portion of the hard layer 130. Thus, the distortion of the rear fixing module 110 may be prevented, and the wearability for the user may increase.

Both ends of the hard layer 130 may be connected to the rear fixing module 110, and a portion of the hard layer 130 may be connected to the soft layer 140. By connecting the hard layer 130 to the soft layer 140, the distortion of the rear fixing module 110 may be reduced. For example, the central portion of the hard layer 130 may be connected to the soft layer 140. The central portion of the hard layer 130 may be disposed at a longest distance from the rotation axis of the driving module 3 based on a direction perpendicular to the rotation axis of the driving module 3, when compared to remaining portions of the hard layer 130. In detail, a length of a moment arm of a torque generated by the driving module 3 may be maximized at the central portion of the hard layer 130. A force applied to an object by a torque applied to another object may be inversely proportional to a length of a moment arm between the two objects. Thus, by connecting, to the soft layer 140, the central portion of the hard layer 130, at which the length of the moment arm from the rotation axis of the driving module is maximized, an unnecessary force generated by the driving module 3 and applied to a body of the user through the soft layer 140 may be minimized.

The hard layer 130 may include a first unidirectional flexible plate 131, a second unidirectional flexible plate 132, a front fixing plate 135, a first length adjusting portion 136, and a second length adjusting portion 137.

The first unidirectional flexible plate 131 and the second unidirectional flexible plate 132 may have flexibilities in a circumferential direction of the waist of the user, in detail, in outward radial directions from a center of the waist of the user, and may not have flexibilities in other directions. In detail, the first unidirectional flexible plate 131 and the second unidirectional flexible plate 132 may be rigid in a direction vertical to the ground and flexible in a direction horizontal to the ground based on a state in which the user is standing erect. In the foregoing structure, the first unidirectional flexible plate 131 and the second unidirectional flexible plate 132 may be deformed based on the body shape of the user, thereby increasing the wearability for the user. Further, the first unidirectional flexible plate 131 and the second unidirectional flexible plate 132 may not be deformed in other directions, thereby preventing a distortion of the pelvis fixing device 10 caused in response to an operation of the driving module 3.

One side of the first unidirectional flexible plate 131 may be connected to the first rigid frame 114, and another side of the first unidirectional flexible plate 131 may be connected to the front fixing plate 135. The first length adjusting portion 136 may be provided in (or, alternatively, connected to) the front fixing plate 135 to adjust a fastening length of the first unidirectional flexible plate 131. In the foregoing structure, by adjusting the fastening length of the first unidirectional flexible plate 131 based on the body shape of the user, a general-purpose utilization of the pelvis fixing device 10 may increase.

Similarly, one side of the second unidirectional flexible plate 132 may be connected to the second rigid frame 115, and another side of the second unidirectional flexible plate 132 may be connected to the front fixing plate 135. The second length adjusting portion 137 may be provided in (or, alternatively, connected to) the front fixing plate 135 to adjust a fastening length of the second unidirectional flexible plate 132. When the first length adjusting portion 136 and the second length adjusting portion 137 are provided on both sides of the front fixing plate 135, a one-sided center of gravity of the pelvis fixing device 10 may be prevented, whereby the wearability for the user may increase.

The layer fastening portion 150 may fasten the soft layer 140 with the hard layer 130. The layer fastening portion 150 may be disposed between an inner side surface of the central portion of the hard layer 130 and an outer side surface of the central portion of the soft layer 140. The layer fastening portion 150 may attach the soft layer 140 to the hard layer 130 and detach the soft layer 140 from the hard layer 130, for example, using a structure of a hook and loop fastener.

The battery 160 may supply a power to drive the driving module 3. For example, the battery 160 may be disposed at a center of the front fixing module 120. In general, the battery 160 may have a relatively great weight. Thus, the weight of the battery 160 may have a great effect on the center of gravity of the pelvis fixing device 10. As a result of performing a simulation using an actual muscular model, for example, Geyer Neuromuscular Model, in a case in which the battery 160 is disposed in the front fixing module 120, a metabolic cost of the user was reduced by about 1 to 1.2%, when compared to a case in which the battery 160 is disposed in the rear fixing module 110.

Further, it was verified that a result of performing a test on real people coincides with the simulation result as shown in Table 1.

TABLE 1

| Category | Walk at 4 km/h | Walk at 6 km/h |
|---|---|---|
| Metabolic cost | Reduced by 1.03% | Reduced by 1.08% |

Such an effect of reducing the metabolic cost is analogous to an effect achieved when the overall weight of the motion assistance apparatus 1 is reduced by about 1 kilogram (kg).

In actuality, a result of surveying a total of 10 subjects showed that the wearability and the weight were relatively excellent in the case in which the battery 160 is disposed in a front portion as described above, when compared to a case in which the battery 160 is disposed in the rear fixing module 110.

A battery and electrical components to be connected to the battery may need to be disposed on a rigid material in terms of a stability issue, for example, disconnection. In the example embodiment, by disposing the hard layer 130 on a front surface of the user, the battery 160 and electrical components to be connected to the battery 160 may be disposed in the hard layer 130. Thus, the stability may be maintained while disposing the battery 160 in the front portion of the user.

The iliac crest pad 170 may be in close contact with an iliac crest of the user, thereby increasing the stability of the pelvis fixing device 10. One side of the iliac crest pad 170 may be connected to a side surface of the rear fixing module 110, another side of the iliac crest pad 170 may be connected to the front fixing module 120, and a central portion of the iliac crest pad 170 may be in close contact with the iliac crest. The iliac crest is a bone positioned around a hip joint. A skin layer around the iliac crest of the user may be relatively thin, compared to other portions of a pelvis and thus, the iliac crest may be a suitable supporter. The iliac crest pad 170 may considerably increase a rigidity of the front fixing module 120.

For example, one side of the iliac crest pad 170 may be connected to the driving module mounting portion 1142, and another side of the iliac crest pad 170 may be connected to the soft layer 140. In the foregoing structure, the iliac crest pad 170 may enable the driving module mounting portion 1142 that directly receives a torque of the driving module 3 to be in close contact with the iliac crest, thereby considerably reducing an effect of the driving module 3 on the stability of the pelvis fixing device 10.

Figure 4:
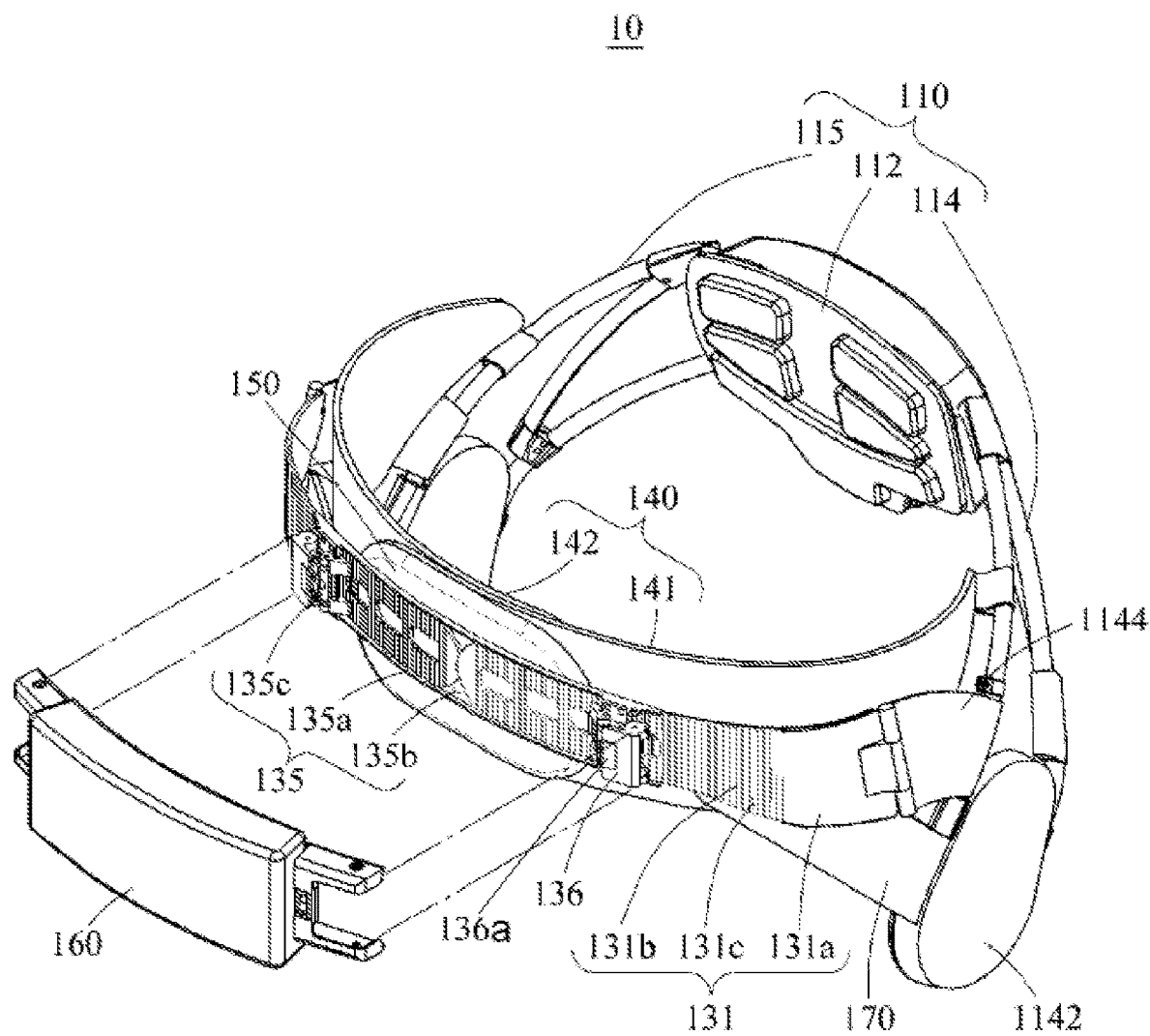
FIG. 4 is a view illustrating a state in which a battery is disconnected from a pelvis fixing device according to at least one example embodiment.

FIG. 4 is a view illustrating a state in which the battery 160 is disconnected from the pelvis fixing device 10 according to at least one example embodiment.

Referring to FIG. 4, the first unidirectional flexible plate 131 may include a flexible plate body 131a, and flexible plate ribs 131b between flexible plate grooves 131c.

One end of the flexible plate body 131a may be connected to the rear fixing module 110, and another end of the flexible plate body 131a may extend lengthwise along the soft layer 140. The flexible plate body 131a may be provided in a form of a thin plate of a rigid material. A width direction of the flexible plate body 131a may be orthogonal to a rotation axis of the driving module 3. The foregoing shape may prevent the first unidirectional flexible plate 131 from being bent in a direction of a torque generated by the driving module 3 while allowing the first unidirectional flexible plate 131 to be bent in a circumferential direction of an abdomen of the user.

The flexible plate ribs 131b may elongate in the width direction of the flexible plate body 131a, and protrude in a direction perpendicular to a longitudinal direction of the flexible plate body 131a. The flexible plate ribs 131b may enhance a rigidness of the first unidirectional flexible plate 131 to prevent the first unidirectional flexible plate 131 from being bent in the direction of the torque generated by the driving module 3.

The flexible plate grooves 131c may be recessed lengthwise in the width direction of the flexible plate body 131a. The flexible plate grooves 131c may increase a flexibility of the first unidirectional flexible plate 131 so that the first unidirectional flexible plate 131 may be bent smoothly in the circumferential direction of the abdomen of the user.

The flexible plate grooves 131c may be spaced between two adjacent flexible plate ribs 131b. Conversely, the flexible plate ribs 131b may be a protrusion between two adjacent flexible plate grooves 131c.

The first length adjusting portion 136 may include a hanging 136a portion to be connected to at least one of a plurality of flexible plate ribs 131b and/or a plurality of flexible plate grooves 131c. In this example, based on a position at which the hanging portion is connected, a fastening length of the first unidirectional flexible plate 131 may be adjusted. In detail, the flexible plate rib 131b and/or the flexible plate groove 131c may be used as a length adjusting device.

The front fixing plate 135 may be disposed at a center of the front surface of the user. The front fixing plate 135 may include a fixing plate body 135a, a battery seating space 135b in which the battery 160 is to be seated, and a battery attaching and detaching portion 135c configured to attach or detach the battery 160.

The fixing plate body 135a may be disposed at a center of a front portion of the soft layer 140. The fixing plate body 135a and the soft layer 140 may be attachable and detachable using a structure of a hook and loop fastener. The first length adjusting portion 136 may be provided in the fixing plate body 135a. The first length adjusting portion 136 may adjust the fastening length of the fixing plate body 135a and the first unidirectional flexible plate 131. The battery seating space 135b may be a space on the front surface of the fixing plate body 135a.

The battery attaching and detaching portion 135c may be provided in the fixing plate body 135a to fix the battery 160 in a state in which the battery 160 is seated in the battery seating space 135b. For example, the battery attaching and detaching portion 135c may include an elastic body (e.g. a spring) configured to attach or detach the battery 160 in a snap fastening manner.

Figure 5:
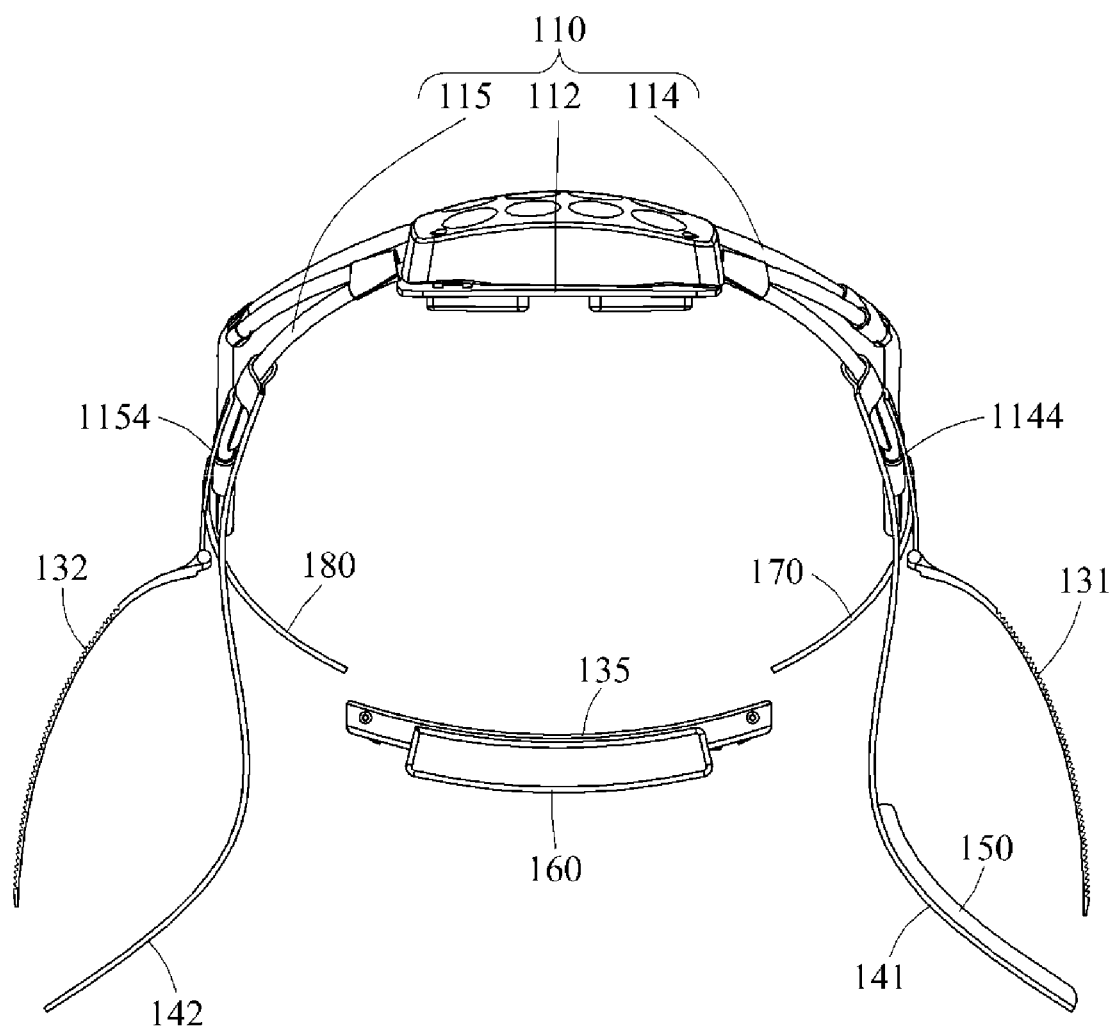
FIG. 5 is a view illustrating a state in which a front fixing module is detached from a pelvis fixing device according to at least one example embodiment.

FIG. 5 is a view illustrating a state in which the front fixing module is detached from the pelvis fixing device 10 according to at least one example embodiment.

Referring to FIG. 5, a user may detach the front fixing module 120 from the pelvis fixing device 10. For example, a user may detach the hard layer 130 of the front fixing module 120 by detaching the first unidirectional flexible plate 131 and/or the second unidirectional flexible plate 132 from the front fixing plate 135. Further, the user may detach the soft layer 140 of the front fixing module 120 by detaching the first soft band 141 and the second soft band 142 from each other. Through the foregoing two-step detaching process, the user may easily remove the pelvis fixing device 10. Conversely, the user may conveniently wear the pelvis fixing device 10 by connecting the soft layer 140 and connecting the hard layer 130 in the state as shown in FIG. 5.

Figure 6:
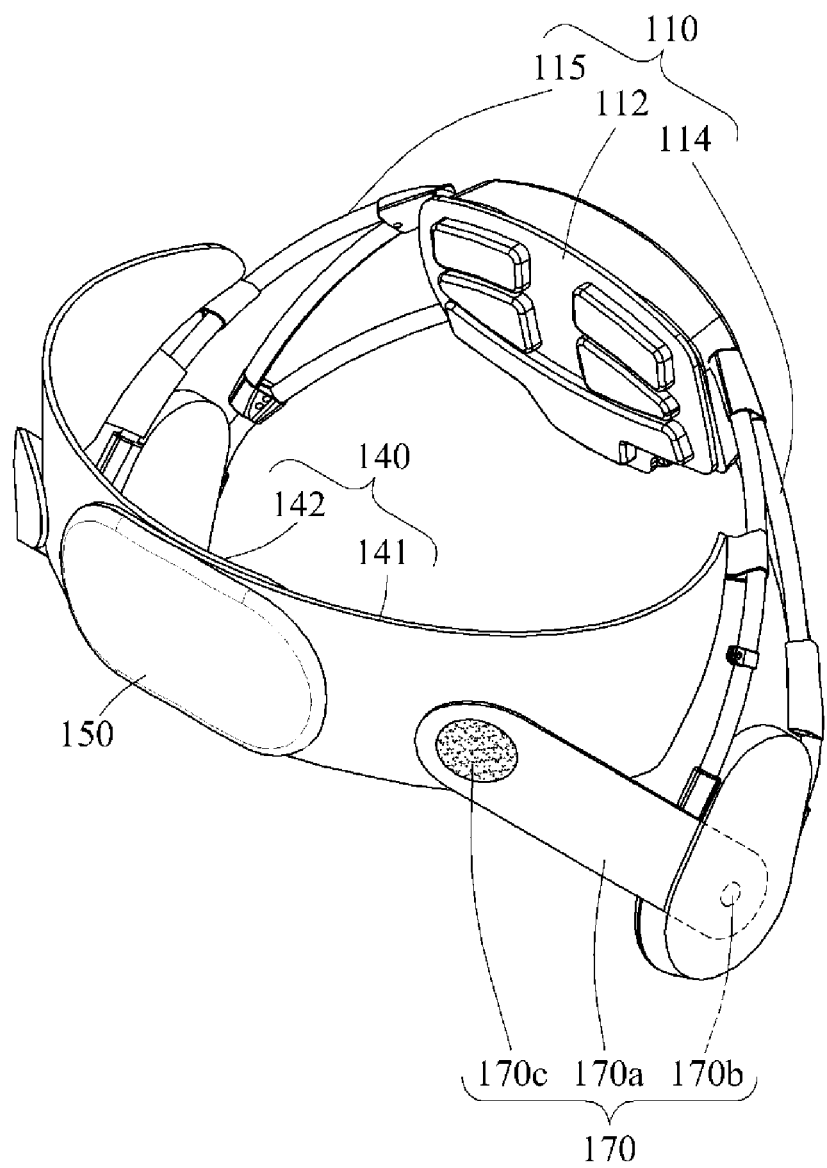
FIG. 6 is a view illustrating a state in which a hard layer is omitted from a pelvis fixing device according to at least one example embodiment.

FIG. 6 is a view illustrating a state in which the hard layer 130 is omitted from the pelvis fixing device 10 according to at least one example embodiment.

Referring to FIG. 6, the iliac crest pad 170 may include a pad body 170a to be in close contact with an iliac crest of the user, a first connecting portion 170b connected to the driving module mounting portion 1142, and a second connecting portion 170c detachable from the soft layer 140. For example, the first connecting portion 170b may have a structure of a hinge, and the second connecting portion 170c may have a structure of a hook and loop fastener. In the foregoing structure, an angle of the iliac crest pad 170 and a position at which the iliac crest pad 170 is attached may be adjusted suitably for a body shape of the user.

Figure 7:
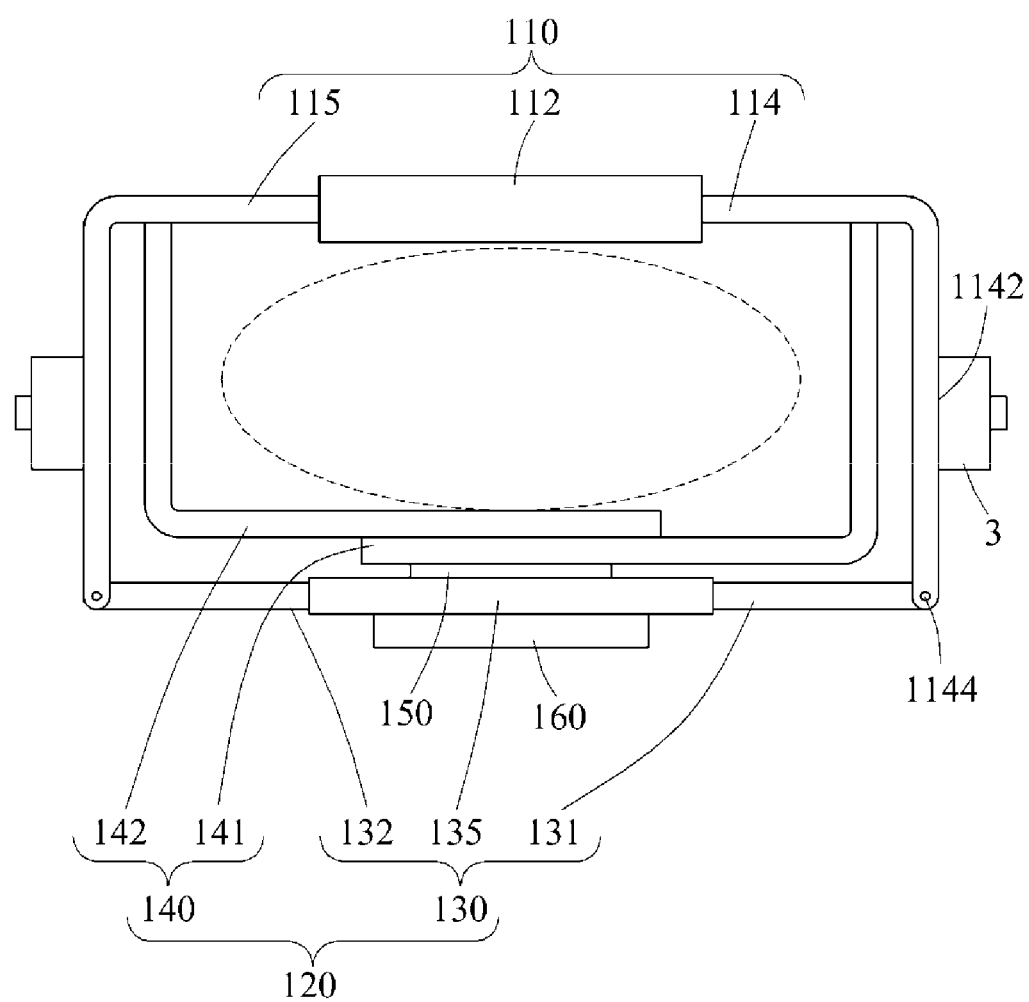
FIG. 7 illustrates a configuration of a pelvis fixing device according to at least one example embodiment.
Figure 8:
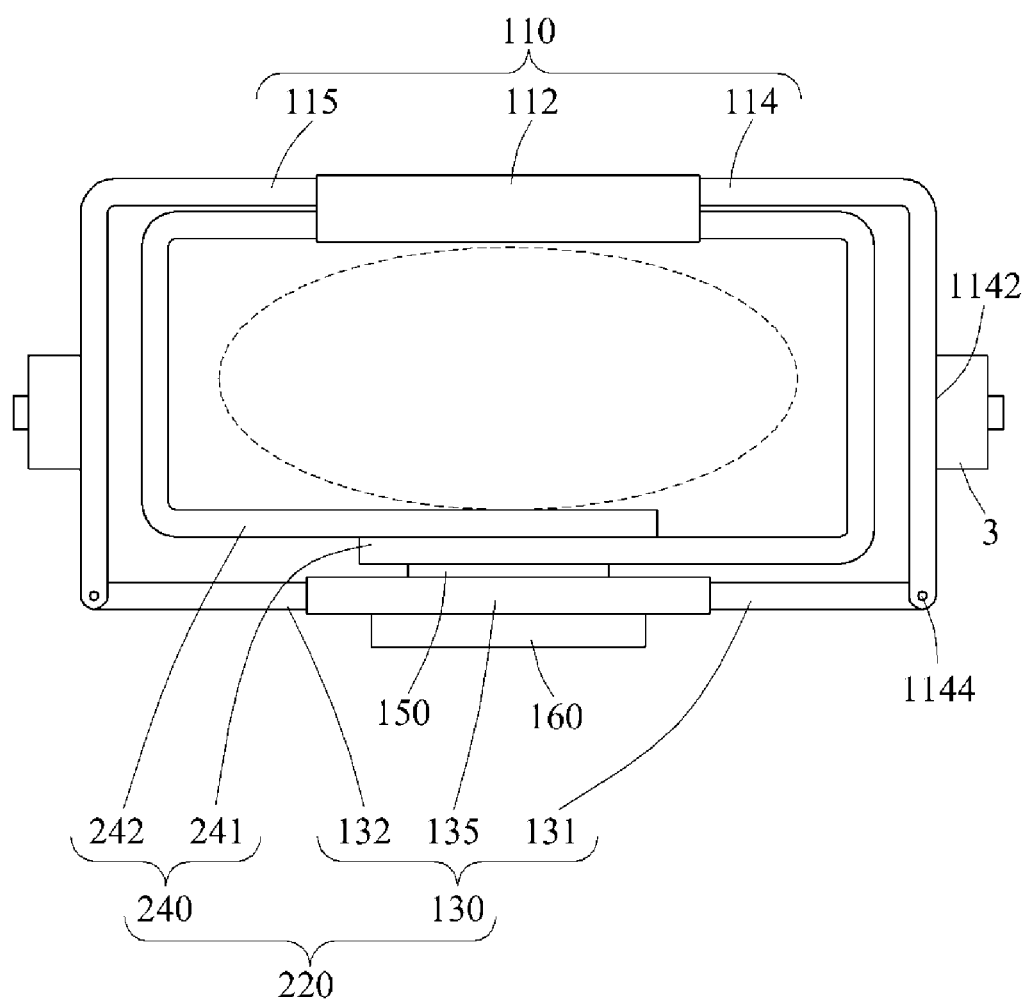
FIG. 8 illustrates a modified pelvis fixing device according to at least one example embodiment.

FIG. 7 illustrates a configuration of the pelvis fixing device 10 according to at least one example embodiment, and FIG. 8 illustrates a modified pelvis fixing device 20 according to at least one example embodiment.

Referring to FIGS. 7 and 8, both end portions of the soft layer 140 may be fixed to the rear fixing module 110. For example, as shown in FIG. 7, one end portion of the soft layer 140 of the pelvis fixing device 10 may be connected to the first rigid frame 114, and another end portion of the soft layer 140 of the pelvis fixing device 10 may be connected to the second rigid frame 115. In another example, both end portions of the soft layer 140 may be connected to two driving module mounting portions, respectively. Further, as shown in FIG. 8, both end portions of a soft layer 240 of the pelvis fixing device 20 may be connected directly to the back supporting portion 112. However, FIGS. 7 and 8 merely illustrate examples of a position at which the soft layer 140 is connected, and example embodiments are not limited thereto.

Figure 9:
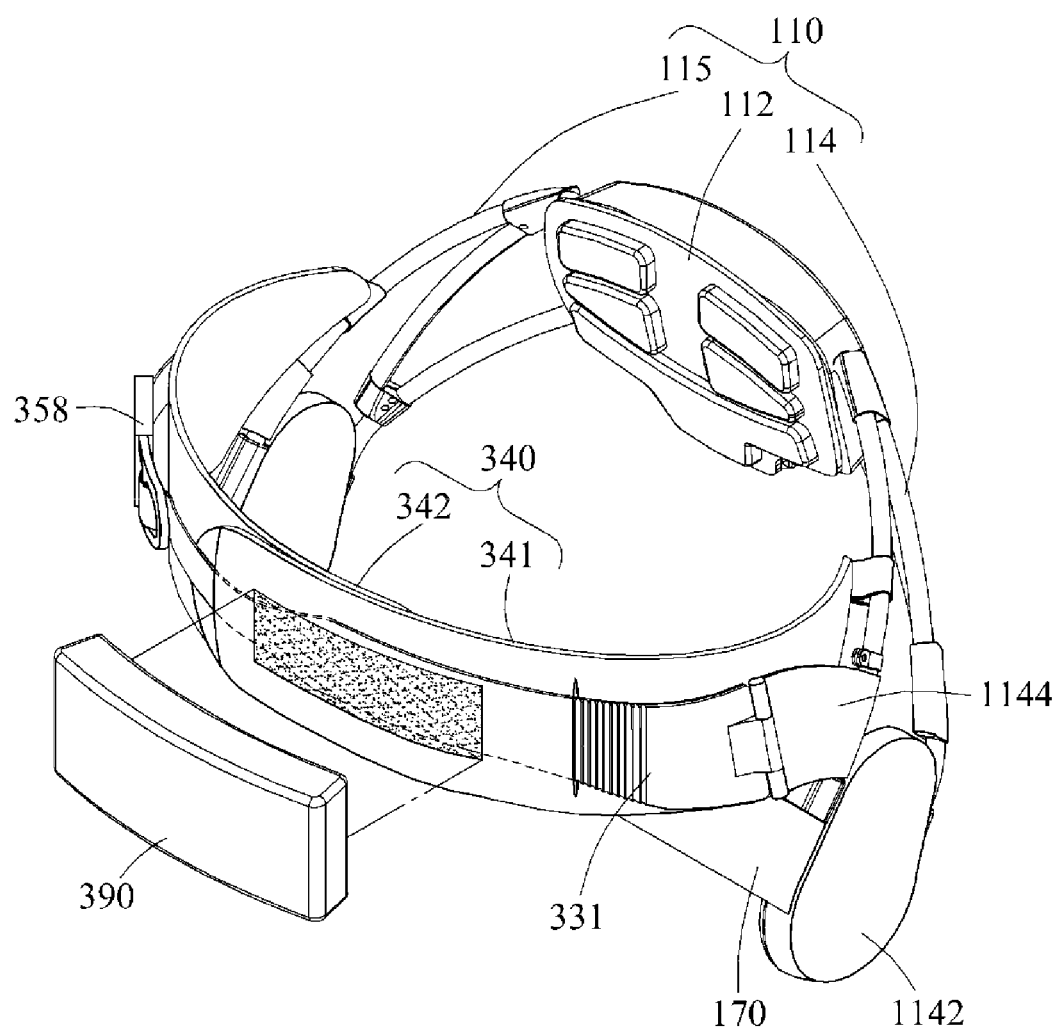
FIG. 9 is a perspective view illustrating a pelvis fixing device according to at least one example embodiment.
Figure 10:
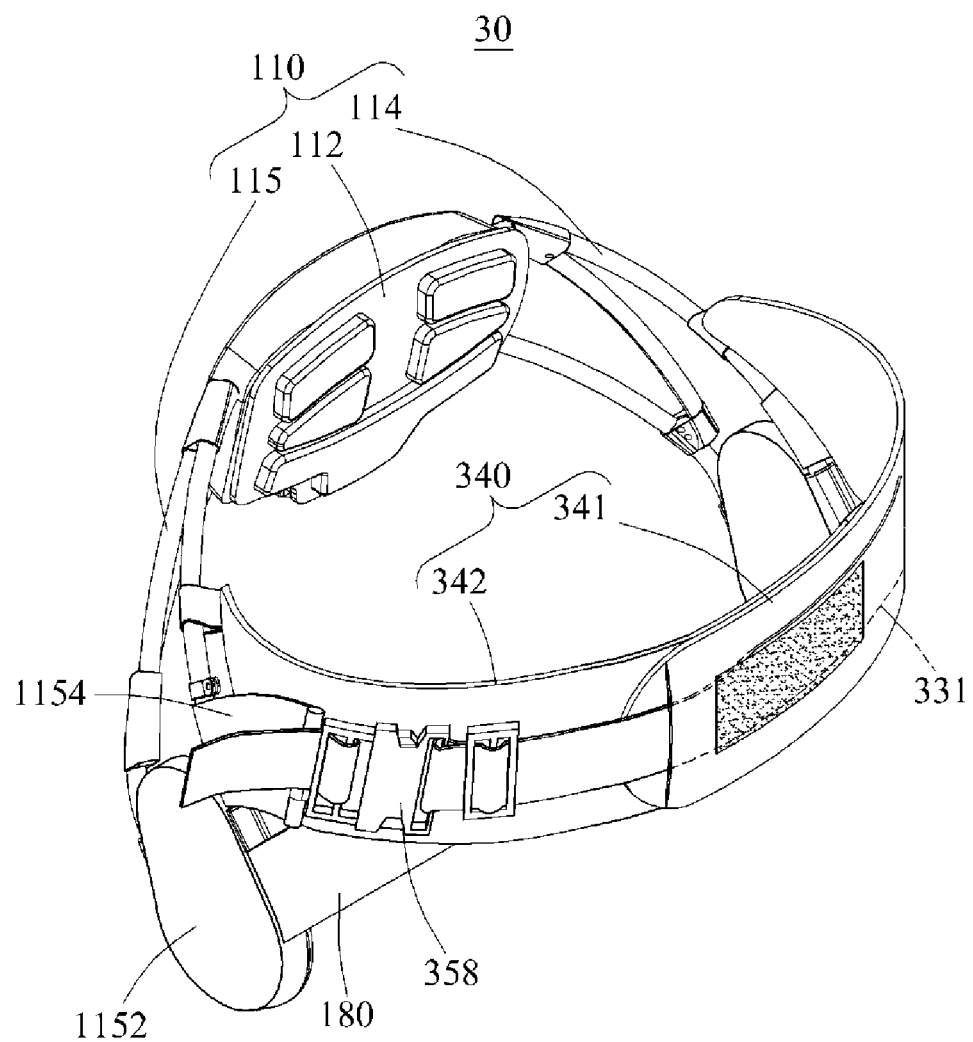
FIG. 10 is a perspective view illustrating a pelvis fixing device viewed from another angle according to at least one example embodiment.

FIG. 9 is a perspective view illustrating a pelvis fixing device 30 according to at least one example embodiment, and FIG. 10 is a perspective view illustrating the pelvis fixing device 30 viewed from another angle according to at least one example embodiment.

Figure 11:
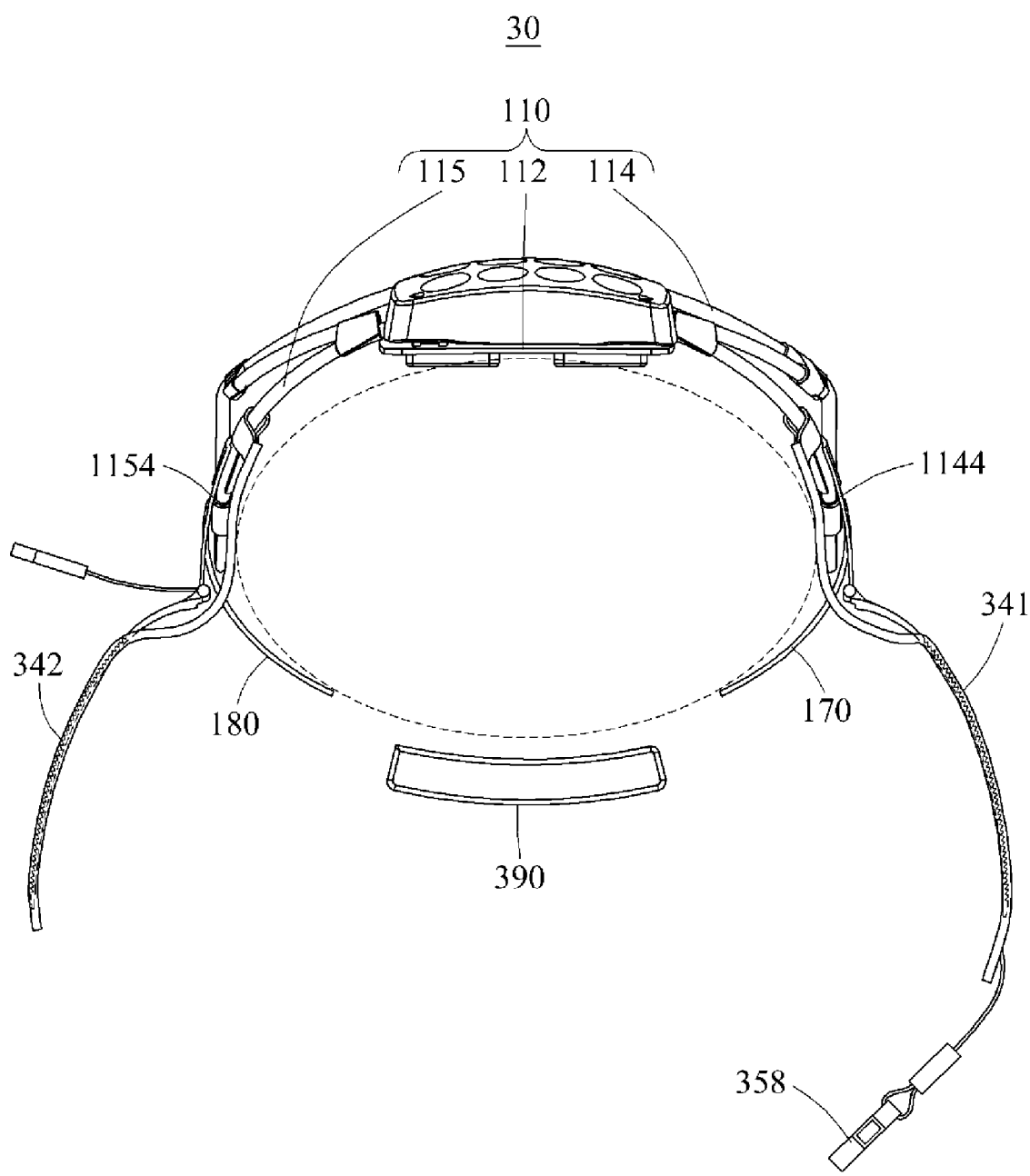
FIG. 11 is a view illustrating a state in which a front fixing module is detached from a pelvis fixing device according to at least one example embodiment.
Figure 12:
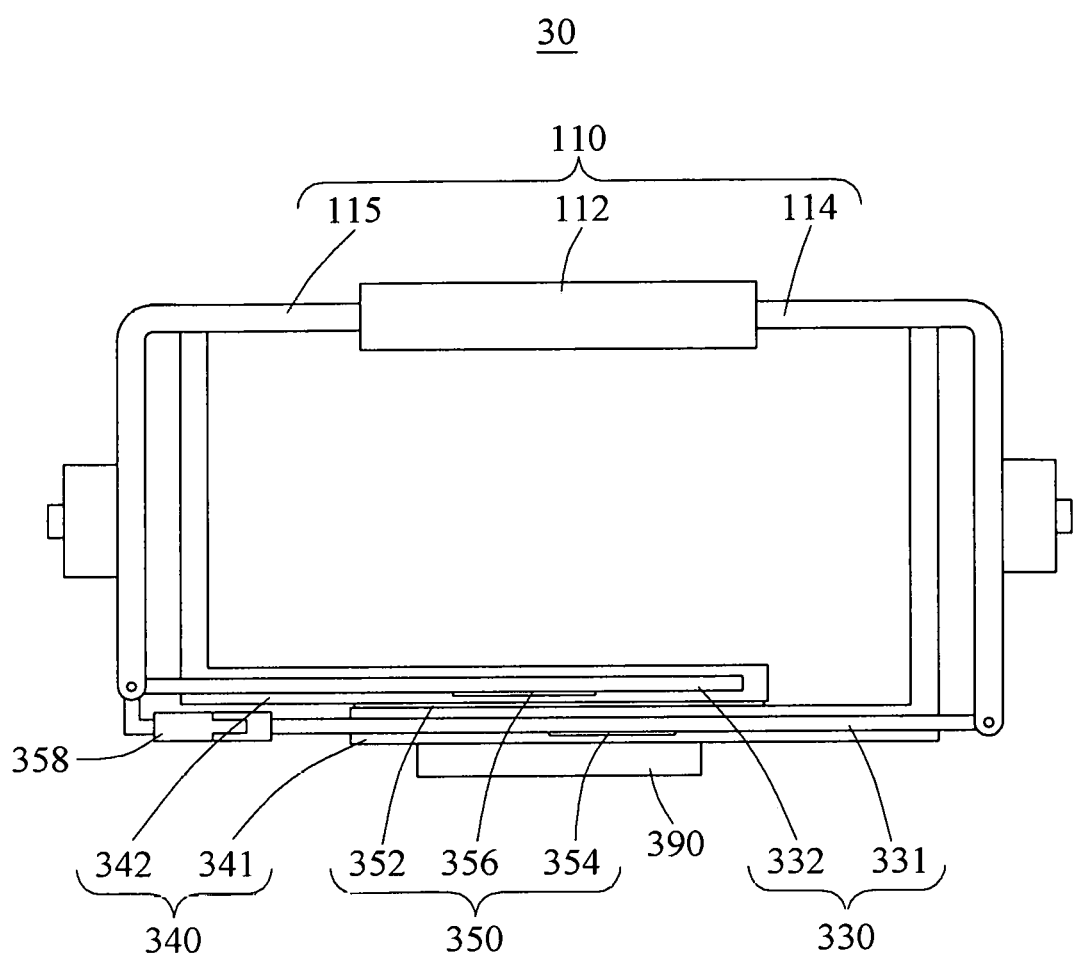
FIG. 12 illustrates a configuration of a pelvis fixing device according to at least one example embodiment.
Figure 13:
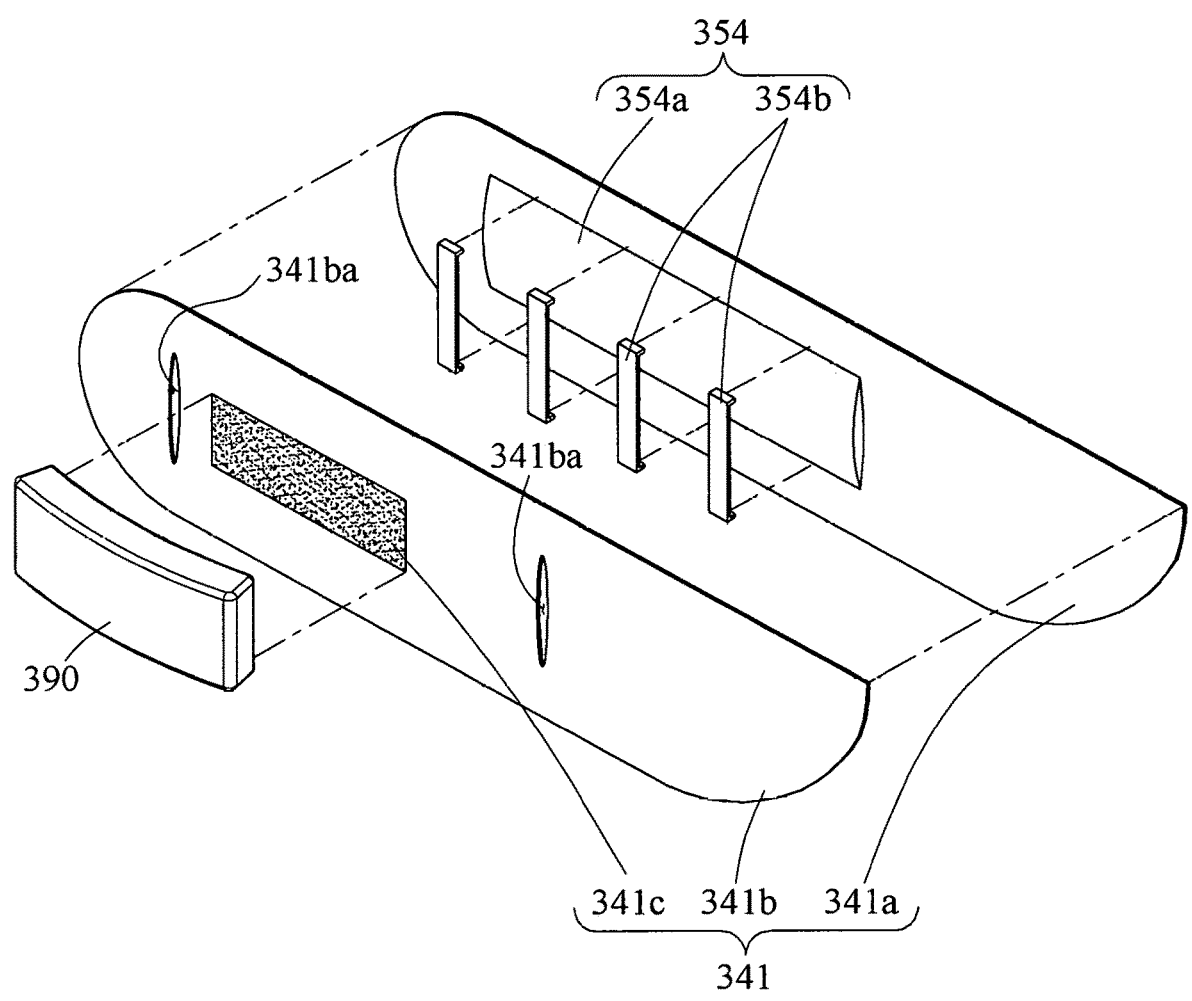
FIG. 13 is an exploded perspective view illustrating a portion of a front fixing module of a pelvis fixing device according to at least one example embodiment.

FIG. 11 is a view illustrating a state in which a front fixing module is detached from the pelvis fixing device 30 according to at least one example embodiment, FIG. 12 illustrates a configuration of the pelvis fixing device 30 according to at least one example embodiment, and FIG. 13 is an exploded perspective view illustrating a portion of the front fixing module of the pelvis fixing device 30 according to at least one example embodiment.

Referring to FIGS. 9 through 13, the pelvis fixing device 30 may include the rear fixing module 110, the front fixing module, a battery 390, and iliac crest pads 170 and 180. The front fixing module may include a hard layer 330, a soft layer 340, and a layer fastening portion 350.

The rear fixing module 110 may include the back supporting portion 112, the first rigid frame 114, and the second rigid frame 115.

At least a portion of the hard layer 330 may be inserted in the soft layer 340. In this example, a user may wear or remove the pelvis fixing device 30 through a process of attaching or detaching the soft layer 340 as shown in FIG. 11.

The hard layer 330 may include a first unidirectional flexible plate 331, and a second unidirectional flexible plate 332.

The soft layer 340 may include a first soft band 341, and a second soft band 342. The first unidirectional flexible plate 331 may be inserted in the first soft band 341, and the second unidirectional flexible plate 332 may be inserted in the second soft band 342. A band fastening portion 352 may be provided between the first soft band 341 and the second soft band 342. For example, the band fastening portion 352 may attach the first soft band 341 to the second soft band 342 and detach the first soft band 341 from the second soft band 342 through a structure of a hook and loop fastener. In the foregoing structure, the hard layer 330 and the rear fixing module 110 may form a closed loop around a waist of the user.

The first soft band 341 may include a lining 341a to be in close contact with a front surface of the user, an upper 341b configured to enclose the lining 341a, and a battery fastening portion 341c disposed on the upper 341b.

The lining 341a may be formed using, for example, a soft material, thereby increasing a degree of contact. The upper 341b may be formed using a material with a less flexibility than the lining 341a. For example, the upper 341b may be formed using a material with little flexibility, thereby increasing stability of the battery 390 and an electrical component to be connected to the battery 390.

An inserting space in which the first unidirectional flexible plate 331 is inserted may be provided between the lining 341a and the upper 341b. Inserting slots 341ba may be formed in the upper 341b. The first unidirectional flexible plate 331 may be inserted in the inserting slots 341ba. At least a portion of the first unidirectional flexible plate 331 may be inserted through the inserting slots 341ba to be disposed in the inserting space. A first inserting slot of the two inserting slots 341ba may be connected to an entrance portion of a fabric tunnel 354a, and a second inserting slot of the two inserting slots 341ba may be connected to an exit portion of the fabric tunnel 354a. The first unidirectional flexible plate 331 may be inserted in the fabric tunnel 354a through the first inserting slot, and connected to an additional fastening portion 358 through the second inserting slot.

The battery 390 may be attached to and detached from the battery fastening portion 341c. In detail, the battery 390 may be attached to a front portion of the pelvis fixing device 30 through the battery fastening portion 341c. The battery fastening portion 341c may be provided in a structure of a hook and loop fastener. However, example embodiments are not limited thereto.

The second soft band 342 may have a structure similar to that of the first soft band 341. Thus, detailed descriptions thereof will be omitted for conciseness.

The layer fastening portion 350 may include a band fastening portion 352 configured to fasten the first soft band 341 with the second soft band 342, a first flexible plate supporting portion 354 configured to support the first unidirectional flexible plate 331 in the first soft band 341, a second flexible plate supporting portion 356 configured to support the second unidirectional flexible plate 332 in the second soft band 342, and the additional fastening portion 358 configured to fasten the first unidirectional flexible plate 331 to the rear fixing module 110.

The first flexible plate supporting portion 354 may support the first unidirectional flexible plate 331 inserted between the lining 341a and the upper 341b. The first flexible plate supporting portion 352 may include the fabric tunnel 354a, and a stiffener 354b.

The first unidirectional flexible plate 331 may be inserted in the fabric tunnel 354a. For example, the fabric tunnel 354a may be formed using a nonflexible material. The fabric tunnel 354a may be formed using a less flexible material than the lining 341a. The fabric tunnel 354a may be disposed in a space between the lining 341a and the upper 341b, and configured to elongate in a longitudinal direction of the first soft band 341. In the foregoing structure, the first unidirectional flexible plate 331 may slide in a longitudinal direction of the fabric tunnel 354a, and be bent in a circumferential direction of an abdomen of the user. However, the first unidirectional flexible plate 331 may not be bent or move in a direction perpendicular to the longitudinal direction of the fabric tunnel 354a.

Dissimilar to the drawings, the fabric tunnel 354a may be a space formed between the lining 341a and the upper 341b, rather than being formed using a separate material. Further, the lining 341a, the upper 341b, and the fabric tunnel 354a may be formed as an integral body using the same material.

The stiffener 354b may increase a supporting force of the fabric tunnel 354a. The stiffener 354b may be formed using a more rigid material than the fabric tunnel 354a, for example, a plastic material. A plurality of stiffeners 354b may be disposed to be spaced apart from each other in the longitudinal direction of the fabric tunnel 354a.

The second flexible plate supporting portion 356 may have a structure similar to that of the first flexible plate supporting portion 354. Thus, detailed descriptions thereof will be omitted for conciseness.

The additional fastening portion 358 may connect the first unidirectional flexible plate 331 to the second rigid frame 115. The additional fastening portion 358 may include a pair of detachable buckles, and a length-adjustable belt connected to the buckles.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A pelvis fixing device comprising:
a rear fixing module configured to enclose a side surface and a rear surface of a waist of a user, the rear fixing module including a driving module mounting portion configured to support a driving module mounted thereto, a first rigid frame and a second rigid frame configured to be connected to the rear fixing module, the first rigid frame and the second rigid frame extending in different directions from the rear fixing module;
a front fixing module configured to enclose a front surface of the waist of the user, the front fixing module including a soft layer and a hard layer, the hard layer configured to connect to the rear fixing module such that closed loops are formed around the waist of the user, the hard layer being rigid in a vertical direction relative to the waist of the user and flexible in a back-and-forth direction relative to the waist of the user, the soft layer including a first soft band and a second soft band each having a first side and a second side, the first side of the first soft band being directly attached to the first rigid frame, the first side of the second soft band being directly attached to the second rigid frame; and
a band fastening portion configured to attach the second side of the first soft band to the second side of the second soft band,
wherein the soft layer extends from the rear fixing module,
wherein the hard layer includes a fixing plate at the soft layer, a first unidirectional flexible plate and a second unidirectional flexible plate, the fixing plate including a first length adjusting portion and second first length adjusting portion to adjust a fastening length of the first unidirectional flexible plate and the second unidirectional flexible plate, respectively,
wherein a first side of the first unidirectional flexible plate is configured to be connected to the first rigid frame, and a second side of the first unidirectional flexible plate is configured to be connected to the first length adjusting portion,
wherein a first side of the second unidirectional flexible plate is configured to be connected to the second rigid frame, and a second side of the second unidirectional flexible plate is configured to be connected to the second length adjusting portion,
wherein the first soft band and the second soft band overlap each other in the back-and-forth direction relative to the waist of the user, and
wherein the first unidirectional flexible plate and the second unidirectional flexible plate overlap each other in the back-and-forth direction relative to the waist of the user.

2. The pelvis fixing device of claim 1, wherein the first and second unidirectional flexible plates are rigid in a vertical direction with respect to a ground and flexible with respect to a horizontal direction to the ground based on a state in which the user is standing erect.

3. The pelvis fixing device of claim 2, wherein each of the first and second unidirectional flexible plates comprises:
a flexible plate body having a first end and a second end, the first end of the flexible plate body being connected to the rear fixing module, and the second end of the flexible plate body being configured to extend lengthwise along the soft layer; and
a flexible plate rib extending from the flexible plate body, the flexible plate rib configured to elongate in a direction perpendicular to a longitudinal direction of the flexible plate body.

4. The pelvis fixing device of claim 3, wherein
each of the first and second unidirectional flexible plates includes a plurality of flexible plate ribs spaced apart from each other in the longitudinal direction of the flexible plate body,
each of the first and second length adjusting portions include a hanging portion configured to connect to at least one of the flexible plate ribs such that the fastening length of the first and second unidirectional flexible plates vary based on which one of the flexible plate ribs is connected to the hanging portion.

5. The pelvis fixing device of claim 1, wherein the first unidirectional flexible plate and the second unidirectional flexible plate run within the soft layer.

6. The pelvis fixing device of claim 5, further comprises:
a plurality of flexible plate supporting portions configured to support respective ones of the first and second unidirectional flexible plates so that the first and second unidirectional flexible plates slide in a longitudinal direction of the soft layer.

7. The pelvis fixing device of claim 6, wherein the plurality of flexible plate supporting portions each comprise:
a fabric tunnel provided in the longitudinal direction of the soft layer, the fabric tunnel configured to have the respective ones of the first and second unidirectional flexible plates inserted therein; and
a plurality of stiffeners spaced apart from each other in a longitudinal direction of the fabric tunnel.

8. The pelvis fixing device of claim 7, further comprising:
first inserting slots configured to receive the respective ones of the first and second unidirectional flexible plates, the first inserting slots being connected to an entrance portion of the fabric tunnel.

9. The pelvis fixing device of claim 8, further comprising:
second inserting slots connected to an exit portion of the fabric tunnel, and additional fastening portions configured to connect the respective ones of the first and second unidirectional flexible plates to the rear fixing module through the second inserting slots.

10. The pelvis fixing device of claim 1, further comprising:
an iliac crest pad between the rear fixing module and the front fixing module.

11. The pelvis fixing device of claim 10, wherein the iliac crest pad comprises:
a pad body configured to closely contact an iliac crest of the user;
a first connecting portion connected to the driving module mounting portion; and
a second connecting portion detachable from the front fixing module.

12. A motion assistance apparatus comprising:
a driver configured to generate a power to assist a motion of a user;
a support connected to the driver, the support configured to support a portion of the user; and
a pelvis fixing device including,
a rear fixing module including a driver mounting portion configured to support the driver, the rear fixing module including a driving module mounting portion, a first rigid frame and a second rigid frame configured to be connected to the rear fixing module, the first rigid frame and the second rigid frame extending in different directions from the rear fixing module, and
a front fixing module connected to both ends of the rear fixing module, the front fixing module including a soft layer, a hard layer, and a fastener therebetween, the soft layer and the hard layer having different rigidnesses, the hard layer configured to connect to the rear fixing module such that closed loops are formed around a waist of the user, the hard layer being rigid in a vertical direction relative to the waist of the user and flexible in a back-and-forth direction relative to the waist of the user, the soft layer including a first soft band and a second soft band each having a first side and a second side, the first side of the first soft band being directly attached to the first rigid frame, the first side of the second soft band being directly attached to the second rigid frame; and
a band fastening portion configured to attach the second side of the first soft band to the second side of the second soft band,
wherein the soft layer extends from the rear fixing module,
wherein the hard layer includes a fixing plate at the soft layer, a first unidirectional flexible plate and a second unidirectional flexible plate, the fixing plate including a first length adjusting portion and second first length adjusting portion to adjust a fastening length of the first unidirectional flexible plate and the second unidirectional flexible plate, respectively,
wherein a first side of the first unidirectional flexible plate is configured to be connected to the first rigid frame, and a second side of the first unidirectional flexible plate is configured to be connected to the first length adjusting portion,
wherein a first side of the second unidirectional flexible plate is configured to be connected to the second rigid frame, and a second side of the second unidirectional flexible plate is configured to be connected to the second length adjusting portion,
wherein the first soft band and the second soft band overlap each other in the back-and-forth direction relative to the waist of the user, and
wherein the first unidirectional flexible plate and the second unidirectional flexible plate overlap each other in the back-and-forth direction relative to the waist of the user.

13. The motion assistance apparatus of claim 12, wherein the first unidirectional flexible plate and the second unidirectional flexible plate have a plurality of flexible ribs therein spaced apart from each other in a longitudinal direction.

14. The motion assistance apparatus of claim 13, wherein the front fixing module is configured to connect to one of the plurality of flexible ribs in each of the first and second unidirectional flexible plates such that a circumference of the pelvis fixing device varies based on which of the plurality of flexible ribs is connected to the fixing plate.

* * * * *